United States Patent
Dandekar et al.

(10) Patent No.: US 6,180,846 B1
(45) Date of Patent: Jan. 30, 2001

(54) PROCESS AND APPARATUS USING PLATE ARRANGEMENT FOR COMBUSTIVE REACTANT HEATING

(75) Inventors: Hemant W. Dandekar, Roselle; Robert C. Mulvaney, III, Arlington Heights, both of IL (US)

(73) Assignee: UOP LLC, Des Plaines, IL (US)

( * ) Notice: Under 35 U.S.C. 154(b), the term of this patent shall be extended for 0 days.

(21) Appl. No.: 09/149,849

(22) Filed: Sep. 8, 1998

(51) Int. Cl.[7] .............................. C07C 1/02; C07C 5/367; C01B 1/00; F28D 7/00; B01J 8/02
(52) U.S. Cl. ..................... 585/443; 423/659; 422/198; 422/138; 422/200; 422/222; 422/236; 585/911; 585/921; 585/924; 252/373
(58) Field of Search ..................... 252/373; 423/659; 422/198, 138, 200, 222, 236; 585/911, 443, 921, 924

(56) References Cited

U.S. PATENT DOCUMENTS

| | | | |
|---|---|---|---|
| 4,127,389 | 11/1978 | Hackemesser et al. | 422/201 |
| 4,442,020 | 4/1984 | Fuderer | 252/373 |
| 4,599,471 | * 7/1986 | Ward | 585/441 |
| 4,666,680 | 5/1987 | Lewis | 422/191 |
| 4,717,781 | * 1/1988 | Imai et al. | 585/441 |
| 4,750,986 | 6/1988 | Pinto | 208/64 |
| 4,810,472 | 3/1989 | Andrew et al. | 422/197 |
| 4,822,521 | 4/1989 | Fuderer | 252/376 |
| 4,910,228 | 3/1990 | Lywood | 518/703 |
| 4,985,231 | 1/1991 | Lywood | 423/652 |
| 5,130,106 | 7/1992 | Koves | 422/216 |
| 5,300,275 | 4/1994 | Lywood | 422/655 |
| 5,405,586 | 4/1995 | Koves | 422/218 |
| 5,512,599 | 4/1996 | Hiramatsu et al. | 517/703 |
| 5,525,311 | 6/1996 | Girod et al. | 422/200 |
| 5,785,942 | * 7/1998 | Hippel et al. | 423/376 |

* cited by examiner

*Primary Examiner*—Tom Dunn
*Assistant Examiner*—Jonas N. Strickland
(74) *Attorney, Agent, or Firm*—John G. Tolomei; Benjamin C. Spehlmann

(57) ABSTRACT

A process and apparatus for indirectly heating an endothermic reaction by combustion of reactants or products from the endothermic reaction using a plate heat exchange arrangement in a highly efficient manner. This invention is particularly suited for processes such as the production of styrene or synthesis gas. When producing synthesis gas, oxidizing reactants in a secondary reforming step generates heat for a primary reforming step and the process improves selectivity and yield with a highly efficient heat exchange step that uses narrow channel for indirect heat exchange. The narrow channels are preferably defined by corrugated plates. The primary reaction channels will contain a catalyst for the promotion of the primary reaction such as steam reforming or ethylbenzene dehydrogenation. The secondary heating step may be performed outside of the heat exchange channels with hot effluent gases passing through the heat exchange channels to provide heat to the primary reaction step or the secondary reaction channels may contain combustion promoting catalyst to generate the heat in-situ.

27 Claims, 9 Drawing Sheets

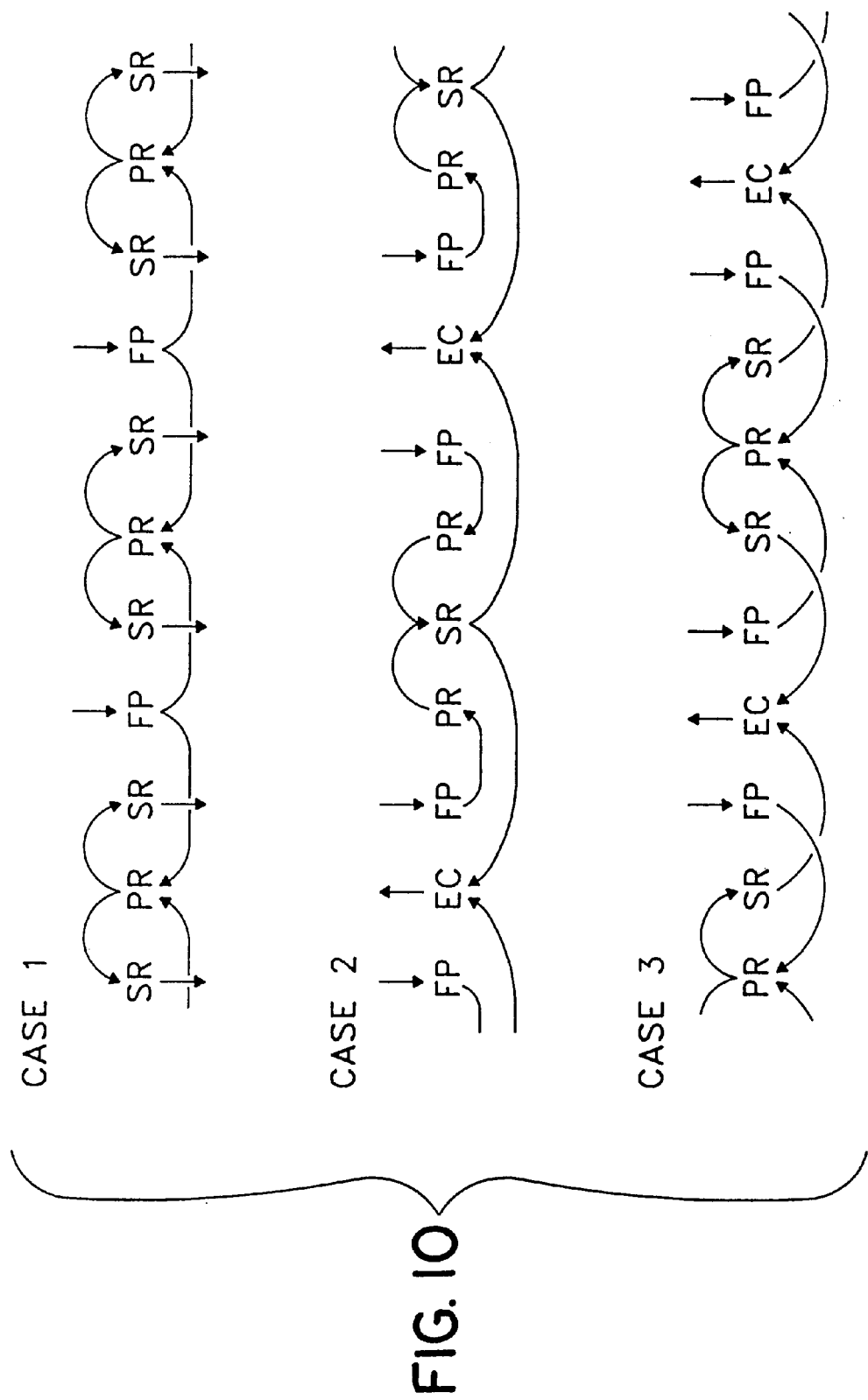

PROCESS AND APPARATUS USING PLATE ARRANGEMENT FOR COMBUSTIVE REACTANT HEATING

FIELD OF THE INVENTION

This invention relates generally to plate type exchangers for indirect heat exchange and the production of synthesis gas by steam reforming and more specifically to their advantageous integration.

BACKGROUND OF THE INVENTION

In many industries, like the petrochemical and chemical industries, contact of reaction fluids with a catalyst in a reactor under suitable temperature and pressure conditions effects a reaction between the components of one or more reactants in the fluids. Most of these reactions generate or absorb heat to various extents and are, therefore, exothermic or endothermic. The heating or chilling effects associated with exothermic or endothermic reactions can positively or negatively affect the operation of the reaction zone. The negative effects can include among other things: poor product production, deactivation of the catalyst, production of unwanted by-products and, in extreme cases, damage to the reaction vessel and associated piping. More typically, the undesired effects associated with temperature changes will reduce the selectivity or yield of products from the reaction zone.

Processes for the production of hydrogen and carbon oxides by reforming methane in the presence of steam or carbon oxides have been practiced for many years. The steam reforming process is particularly well known, and involves passage of a mixture of feedstock and steam over a steam reforming catalyst. Typical steam reforming catalyst comprises nickel and may include cobalt on refractory supports such as alpha alumina or calcium aluminate. The strong endothermic nature of the primary steam reforming reaction requires a supply of heat to maintain the reaction. Those skilled in the art routinely balance the endothermic heat requirements of the primary reforming reaction with a partial oxidation of hydrocarbons to provide a secondary reforming reaction that supplies heat for the primary reforming stage and generates additional synthesis gas. Extensive and highly developed teachings detail methods of indirectly exchanging heat between primary and secondary reforming zones. The operation of an adiabatic reformer for synthesis gas production is shown in U.S. Pat. Nos. 4,985,231. 5,300,275 sets forth another basic arrangement that uses a secondary reforming reaction to supply hot gas for heating the primary reforming reaction. U.S. Pat. Nos. 4,810,472; 4,442,020; 4,750,986; and 4,822,521 disclose particular arrangements of heat exchange reactors that indirectly exchange heat between hot gases from the secondary reforming stage and the primary reforming stage. U.S. Pat. No. 4,127,389 shows a variety of tube chamber designs for supplying heat to a primary reforming reaction from a secondary reforming reaction zone. As established by the above referenced patents, the art currently relies exclusively on tube arrangements, and most commonly relies on double walled tubes referred to as "bayonet tubes, for exchanging heat between the primary and secondary reforming zones. The geometry of tubular reactors poses layout constraints that require large reactors and a vast tube surface to achieve high heat transfer efficiencies.

Other process applications accomplish indirect heat exchange with thin plates that define channels. The channels alternately retain catalyst and reactants in one set of channels and a heat transfer fluid in adjacent channels for indirectly heating or cooling the reactants and catalysts. Heat exchange plates in these indirect heat exchange reactors can be flat or curved and may have surface variations such as corrugations to increase heat transfer between the heat transfer fluids and the reactants and catalysts. Many hydrocarbon conversion processes will operate more advantageously by maintaining a temperature profile that differs from that created by the heat of reaction. In many reactions, the most beneficial temperature profile will be obtained by maintaining substantially isothermal conditions. In some cases, a temperature profile directionally opposite to the temperature changes associated with the heat of reaction will provide the most beneficial conditions. For such reasons it is generally known to contact reactants with a heat exchange medium in cross flow, cocurrent flow, or countercurrent flow arrangements. A specific arrangement for heat transfer and reactant channels that offers more complete temperature control can be found in U.S. Pat. No. 5,525,311; the contents of which are hereby incorporated by reference. Other useful plate arrangements for indirect heat transfer are disclosed in U.S. Pat. Nos. 5,130,106 and 5,405,586.

Long sought objectives of reforming processes for the production of synthesis gas are the provision of highly efficient heat exchange and a reduction of fuel requirements which in turn serve to raise product yields from the process. Efficient heat exchange with the secondary reforming zone can provide a potentially auto thermal process. Conversion of hydrocarbons from the feed or primary reforming zone effluent in the secondary reforming zone presents an additional yield loss to the extent that oxidation produces heat rather than desired products. In particular, large quantities of hydrogen or an ammonia synthesis mixture of hydrogen and nitrogen can be produced by steam reforming operations or by the partial oxidation reactions. The synthesis gas streams are typically produced for use as feedstocks in downstream processing such as the production of methanol, formaldehyde, or dimethyl ether.

Variations in the reactor operations, the composition of the feed, and amount of the feed sent to the primary versus the secondary reforming zone can be used to control the $H_2$:CO ratios Ts generated in the reformer effluent. Adjusting the $H_2$:CO to suit the stoichiometry requirements of downstream processing improves process integration. The principal shift reaction of methane and steam to CO and $H_2$ in the primary reforming reaction produces a 3:1 $H_2$:CO ratio. Partial oxidation of methane in the secondary reaction produces a 2:1 $H_2$:CO ratio. Over oxidation converts $H_2$ and CO to undesired water and $CO_2$. Dependence on the secondary reforming reaction to produce heat restricts variations in the feeds and operating conditions, limits the range of $H_2$:CO ratios that may be obtained in the synthesis gas effluent, and interferes with the supply of a synthesis gas to a downstream processing reaction with the desired stoichiometric $H_2$:CO ratio. U.S. Pat. Nos. 4,910,228 and 5,512,599 are particularly directed to achieving a desired heat integration to provide a secondary reforming gas having the approximate stoichiometric requirement of a feed for downstream methanol production.

The production of synthesis gas may find particular utility in the supply of feed to produce methanol or higher hydrocarbons from methane by methods such as the Fisher Tropsch process. Facilitating the production of hydrocarbon synthesis feeds can promote the utilization of the large proportion of natural gas that typically accompanies the discovery of petroleum reserves. Most of these reserves are discovered in remote areas where transportation of low molecular weight gas proves uneconomical. Accordingly, there is a need for compact and efficient equipment that is easily transported to, and operated in, the isolated oil fields where the natural gas is found.

It is, therefore, an object of this invention to improve the efficiency of indirect heat transfer from a secondary reforming reaction to a primary reforming reaction.

It is a further object of this invention to reduce the combustion requirements of synthesis gas feeds for supplying heat to a primary reforming reaction.

It is a further object of this invention to reduce the fuel requirements for supplying heat to a primary reforming reaction from a secondary reforming reaction to provide greater control over the ratio of components in synthesis gas product.

It is a yet further object of this invention to provide a greater range of stoichiometric ratios for feedstocks derived from synthesis gas production.

An additional object of this invention is to provide a compact equipment arrangement for the production of syngas from natural gas.

BRIEF SUMMARY OF THE INVENTION

It has now been discovered that a heat exchange arrangement comprising a plurality of plates defining narrow channels for containing a primary reforming reaction will reduce heating gas consumption while also improving selectivity. The improvement in selectivity allows greater control of the synthesis gas composition and thereby facilitates its tailoring to the specific stoichiometric requirements of downstream processing. Narrow channels of the plate arrangement increase the efficiency of the indirect heat transfer from the secondary reforming reaction to the primary reforming reaction such that fuel requirements in the secondary reforming reaction drop appreciably thereby providing the direct benefit of increased savings on fuel costs and the indirect benefit of greater control of the synthesis gas composition produced therein. By this invention it is possible to maintain a broad ratio of carbon monoxide to hydrogen in the synthesis gas. Ratios for H:C produced by this process can range from 1.15 to 2.2. Where the synthesis gas reaction produces a feed for downstream methanol production, the resulting decrease in oxidation also reduces oxygen supply costs. The need for less heat input also preserves a higher $H_2$:CO ratio in the effluent so that the feed can accommodate greater percentages of higher $C_2$ and higher hydrocarbons.

The process also accomplishes a highly efficient utilization of the hydrocarbon passed into the synthesis gas reformers as the feedstock. In the case of methane, this process can achieve a high degree of methane utilization which will usually leave less than 2.5 wt % methane in the synthesis gas product. In many cases the process can achieve a near total methane utilization such that the synthesis gas contains less than 1 wt % methane. Where the feed hydrocarbon has higher carbon numbers, the high thermal efficiency of the process still permits the production of a H:C ratio of 2.0. The desired H:C ratio of 2.0 to 2.2 for methanol production can be achieved with quantities of $C_2$ and higher hydrocarbons that are at least 10 wt % of the feed and can even be achieved where the quantities of $C_2$ and higher hydrocarbons even exceed 12 wt % of the feed. The high thermal efficiency also aids in the maximization of hydrogen production from higher hydrocarbon feeds.

The high heat transfer efficiency provided by the plate arrangement reduces the space required for the reforming reactors and any associated heat exchange equipment. This resulting reduction in equipment dimensions shrinks the overall size of the facilities needed to produce a unit of synthesis gas. The invention thereby fulfills the need for an extremely compact reactor arrangement to supply synthesis gas for the production for more readily transportable fuels such as methanol or distillates.

The presence of narrow heat exchange channels for containing the primary reforming reaction constitutes an essential requirement of this invention. Heating of the heat transfer plates defining the narrow primary reforming reaction channels may occur through the passage of hot gas from a remote secondary reforming reaction or directly from a secondary reforming reaction occurring on the opposite side of the heat exchange plates. With respect to the gas flow through the primary reforming reaction channels gas may flow through the heating channels in countercurrent flow, cocurrent flow, or crosscurrent flow.

Variations in the catalyst loading within the reaction channels for the primary reforming reaction and within the heating channels for delivering heat from the secondary reforming may satisfy different processing objectives. For example, short loading of catalyst in the primary reaction channels can provide a space above or below the primary reforming section in which to preheat feed. Direct generation of heat by the secondary reforming reaction may also be performed in a highly efficient manner by loading catalyst in the heating channels. Again, short loading of the heating channels with the secondary reforming catalyst can provide an additional area of open channels for heat exchange of the secondary reaction effluent with the primary reaction zone or for cooling the effluent from the secondary reaction zone against the feed entering the primary reaction zone.

Another variation on the plate arrangement can use two or more separate stacks of heat exchange plates or "reaction stacks" to conduct different reactions and heat exchange steps in isolated reaction zones. For example, one arrangement of alternating narrow channels in a reaction stack may contain catalyst for the secondary reforming reaction in one set of channels while exchanging heat with the entering feed in another set of channels. A system of manifolds can then pass the isolated preheated feed and secondary steam reforming effluent to another section of heat exchange channels that again indirectly contact the hot gases from the secondary reforming reaction in indirect heat exchange with channels containing catalyst for a primary reforming reaction. Suitable ducting can then return all or any portion of the primary reforming reaction zone effluent to the secondary reforming reaction zone. Integration of the manifolds with external pipes can further enhance process control.

The plates defining the channels for containing the reactions and heat exchange gases may have any configuration that produces narrow channels. A suitable plate arrangement may use relatively smooth plates with intermediate spacers placed intermittently between the plates to preserve the channel space and to introduce turbulence for promoting heat transfer. A spiral wound arrangement of narrowly spaced apart channels can provide a high degree of contacting and heat exchange. A preferred form of the heat exchange elements is relatively flat plates having corrugations defined therein. The corrugations serve to maintain spacing between the plates while also supporting the plates to provide a well supported system of narrow channels. Additional details on the arrangement of such plate systems are shown in U.S. Pat. No. 5,525,311; the contents of which are hereby incorporated by reference.

Suitable plate arrangements may also incorporate perforated plates. Most advantageously, perforated plates would allow the controlled quantities of the primary steam reforming product to flow directly from the primary reforming zone channels as feed into the secondary reforming zone channels. Perforated plates would disperse the introduction of the primary zone effluent over a desired portion of the secondary reforming zone. The normal flow direction of the feed to the primary reforming reaction zone and then to the secondary reforming zone would provide the necessary pressure drop for the flow of primary reforming components into the secondary reforming zone. Those skilled in the art will recognize other variations in plate configurations that can provide additional benefits to the integrated reforming stages.

In a broad process embodiment, this invention contacts reactants with a catalyst in a reaction zone while indirectly heating the reactants by contact with combustion gases formed in a heat producing zone. The process contacts the primary reactant stream with a catalyst for the promotion of an endothermic process in a plurality of narrow channels. Principal spaced apart plates define the narrow channels. Heat exchange with a hot gas stream across the plates that define the reaction channels indirectly heat the feedstock. The process collects a primary effluent from the reaction channels. An oxygen-containing stream that mixes with a portion of the primary effluent stream or a portion of the primary reactant stream passes to an oxidation zone to produce a secondary effluent stream. At least a portion of the secondary effluent stream passes into contact with the principal spaced apart plates to supply the hot gas stream for indirect heat exchange with the reactant channels. The process recovers a product stream comprising at least a portion of the primary effluent stream or the secondary effluent stream.

Accordingly, in an embodiment for a specific reaction, this invention is a process for contacting reactants with a catalyst in a reaction zone while indirectly heating the reactants by contact with combustion gases formed in a heat producing zone. The process comprises contacting a methane-containing stream and a steam-containing stream with steam reforming catalyst in a plurality of narrow reaction channels defined by spaced apart plates. The process indirectly heats the feedstock in the reaction channels by heat exchange with a hot gas stream across the plates that define the reaction channels and collects a primary effluent stream from the heat reaction channels. An oxygen-containing stream passes into contact with at least a portion of the primary effluent stream or a portion of the methane-containing stream in a combustion zone to produce a secondary effluent stream. At least a portion of the secondary effluent stream passes into contact with the plates to supply the hot gas stream for indirect heat exchange with the reaction channels. A synthesis gas comprising at least a portion of the primary effluent stream or the secondary effluent steam is recovered from the process.

In a further specific reaction embodiment, this invention is a process for contacting reactants with a catalyst in a reaction zone while indirectly heating the reactants by contact with combustion gases formed in a heat producing zone. The process comprises contacting a feedstock comprising methane and steam with a steam reforming catalyst in a plurality of narrow reaction channels defined by a plurality of spaced apart plates; indirectly heating the feedstock in the reaction channels by heat exchange with a hot gas stream that passes through heat exchange channels defined by the plates and interleaved with the reaction channels; and collecting a primary effluent stream from the reaction channels, At least a portion of the primary effluent stream passes to a combustion zone and contacts an oxygen-containing stream to produce a secondary effluent stream. At least a portion of the secondary effluent stream passes into contact with the plates defining the heat exchange channels to indirectly heat the reaction channels. The process recovers a synthesis gas comprising at least a portion of the secondary effluent steam.

In a different embodiment, the invention comprises an apparatus for contacting reactants with a catalyst in a reaction zone while indirectly heating the reactants by contact with combustion gases formed in a heat-producing zone. The apparatus comprises a plurality of alternate reaction channels and heat exchange channels defined by a plurality of primary plates. The plates establish a reactant inlet at one end of the heat exchange channels, a reactant outlet at an opposite end of the heat exchange channels, a heating fluid inlet at one end of the heat exchange channels and a heating fluid outlet at the opposite end of the heat exchange channels. Means are provided for retaining a solid catalyst in the reaction channels. A heating fluid conduit communicates the reactant outlet with the heating fluid inlet. The heating fluid conduit or the heat exchange channel define an oxidation zone. An oxygen conduit supplies an oxygen-containing gas to the oxidation zone.

In another specific reactor embodiment, this invention is an apparatus for contacting reactants in a reaction stream with a catalyst in a reaction zone. The apparatus directly heats reactants by combusting a portion of the reaction stream or components produced in the reaction stream in a heating zone while indirectly heating the reactants by contact with combustion gases formed in the heating zone. The apparatus includes a reactor body and a primary plate in the reactor body that defines a first reactor volume with a first plurality of pockets on a first side of the plates and a second reactor volume with a second plurality of pockets on a second side of the plate. One or more first divider plates located in the reactor body extend into at least two pockets in the first plurality of pockets to define at least two pairs of interconnected channels along a first flow path. One or more second divider plates also located in the reactor body extend into at least two pockets in the second plurality of pockets to define pairs of interconnected channels along a second flow path. The reactor body defines an inlet and an outlet for both the first flow path and the second flow path. At least one of the primary plates or the first or second divider plates provides a heat exchange surface. In more specific detail, the primary plate may have any repeating oscillating shape such as a sinusoidal or a sawtooth pattern. A serpentine shape formed from a single plate is particularly preferred. The apparatus is particularly useful for coated plates where all of the divider plates may be attached to a common support plate.

Additional embodiments, arrangements, and details of this invention are disclosed in the following detailed description of the invention.

BRIEF DESCRIPTION OF THE DRAWINGS

FIGS. 10 and 11 are charts showing the placement of heat exchange and reaction zones in channels.

DETAILED DESCRIPTION OF THE INVENTION

Figure 1:
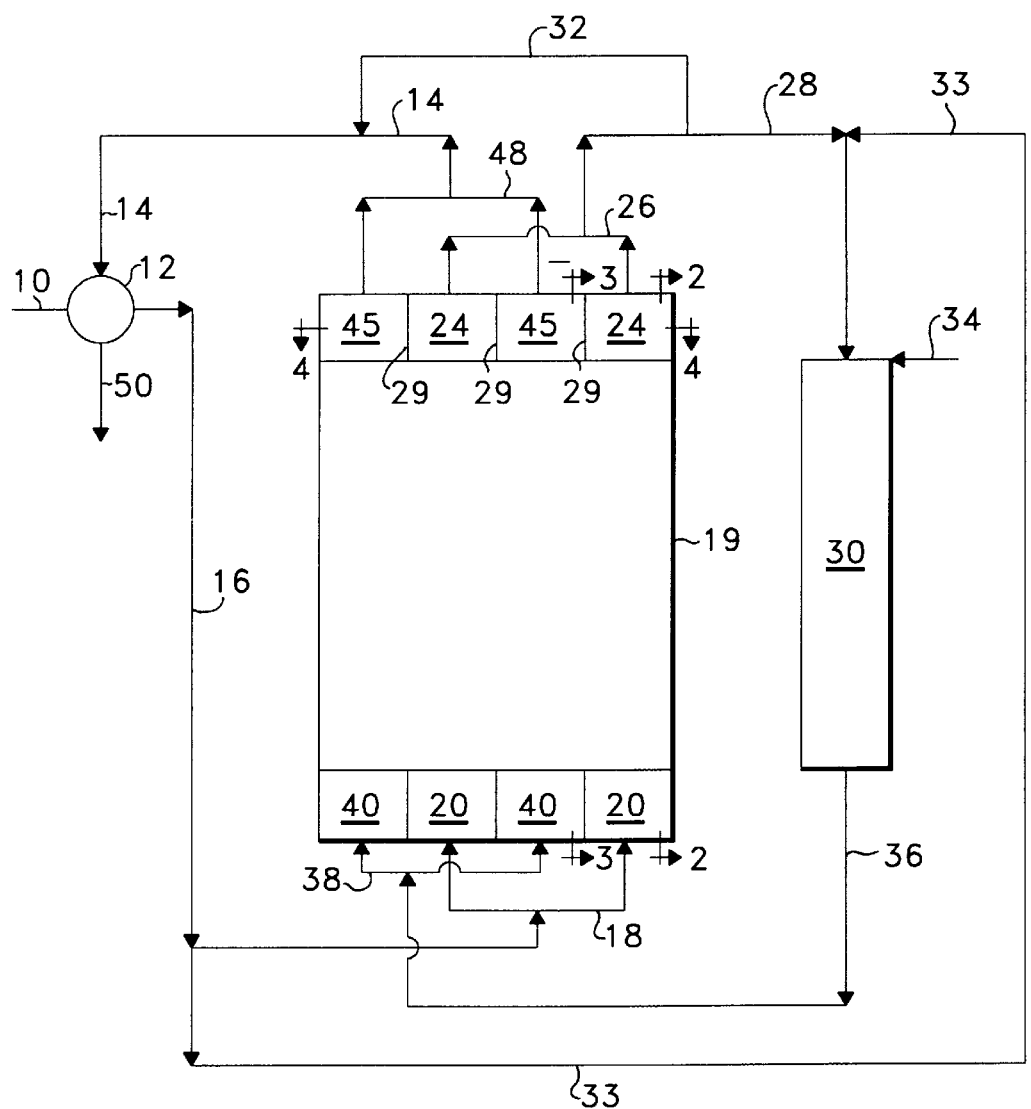
FIG. 1 is a schematic flow diagram of a reactor and heat exchanger arrangement for primary and secondary reforming reactions arranged in accordance with this invention.

This invention may be useful in any autothermic process where the conversion of a reactant or a portion of an endothermically reacted stream provides fuel for an exothermic reaction that heats the endothermic reaction. Additional requirements of this process for compatibility with a plate exchanger arrangement will typically require that there be a relatively low ΔT between the exothermic and endothermic reaction zones along with the relatively low ΔP across the plate sections. Differential temperatures of 200° C. or less are preferred for this invention. Differential pressures preferably will not exceed 0.7 MPa.

Reactions for the production of synthesis gases typically meet these requirements. Suitable reforming reactions for the practice of this invention include production of raw ammonia synthesis gas, production of raw hydrogen streams, and the production of synthesis gas for conversion to organic compounds.

The production of raw ammonia synthesis gas ordinarily includes a primary reforming step of reforming a hydrocarbon feedstock with steam to give a gas containing carbon oxides, hydrogen, methane, and unreacted steam. The effluent from the primary reforming step reacts catalytically with an oxygen- and nitrogen-containing mixture, typically air, to convert additional portions of methane and introduce nitrogen into the product stream. After the shift reaction and $CO_2$ removal, the raw ammonia synthesis gas will have a desirable hydrogen to nitrogen ratio of approximately 2.5 to 3.0. Typical operating temperatures for the production of a raw ammonia synthesis gas are in the range of from 450–600° C. Operating pressures for the production of ammonia from synthesis gas usually lie within a range of from 5 to 10 MPa.

As previously mentioned, another well known reforming operation will produce a raw methanol synthesis gas having desirable stoichiometric ratios for the production of methanol. The general steps of a steam reforming reaction for methanol feed production take place at elevated temperatures and are well known. Operating conditions in the primary reforming stage will be in a temperature range of from 420 to 920° C. The specific operating pressures employed are principally influenced by the pressure requirements of the subsequent processing operations in which the reformed gas mixture is employed. Any super atmospheric pressure can be used in the practice of most reforming operations and is suitable for most applications of the apparatus and process of this invention. Pressures of from about 2 to 5 MPa are commonly employed, although lower pressures can be used, and pressures as high as 10 MPa can be maintained in particular applications.

In the production of synthesis gas, a fluid hydrocarbon such as natural gas is converted to a hot reformed gas mixture containing principally hydrogen and carbon monoxide in this process according to reaction (1) as follows:

$$CH_4 + H_2O \leftrightarrow CO + 3H_2 \tag{1}$$

that is generally known as primary reforming and is widely used in the production of synthesis gas or pure hydrogen. This endothermic reaction is carried out in the practice of this invention, in contravention to conventional practice, by passing a gaseous mixture of fluid hydrocarbon and steam through an externally heated reaction channel packed with a suitable catalyst composition such as solid catalyst granules deposited on an inert carrier material. The necessary heat is supplied by the conventional secondary reforming reaction that oxidizes a fluid hydrocarbon fuel such as a side stream from the fluid hydrocarbon feedstream or a portion of the primary reforming effluent stream. Oxidation supplies the heat to the primary reformer by indirect heat exchange.

The effluent of the primary reforming operation passes, at least in part, to the secondary reformer. In the practice of the invention and in conventional practice, the secondary reforming operation is carried out to react unconverted methane present in the primary reformer effluent with air or other oxygen-containing gases. The following reactions occur in the secondary reforming zone:

$$2CO + O_2 \rightarrow 2 \rightarrow CO_2, \tag{2}$$

$$2CH_4 + O_2 \rightarrow 4H_2 + 2CO, \text{ and} \tag{3}$$

$$2H_2 + O_2 \rightarrow 2H_2O \tag{4}$$

Reactions (2), (3), and (4) are exothermic reactions that tend to occur quite rapidly in the secondary reaction space. As the resulting gas mixture passes through the catalyst bed of the secondary reformer zone, the remaining methane is converted by reaction with steam in accordance with reaction (1) above and by the reaction with oxygen according to reaction (3) above so that very little methane remains in the product gas of the process. The strongly endothermic reaction (1) is a relatively slow reaction that occurs throughout the passage of the gases through the catalyst bed of the secondary reforming zone, thereby cooling the gases from the high temperatures reached by reactions (2), (3), and (4) that occur toward the feed end of the secondary reaction zone. In the practice of the invention, the proportions of oxygen and of the fluid hydrocarbon feed passed to the integrated primary-secondary reformers maintain an essentially, or completely, autothermal process with essentially no fuel requirement. An advantageous feature of the invention is the flexibility of being able to bypass a portion of the hydrocarbon feedstream directly to the secondary reforming reaction space at the feed end of the secondary reforming zone.

The reactant stream contacts a particulate catalyst in each of the reaction stacks. The catalyst employed in the practice of the invention can be any one or more suitable reforming catalysts employed in conventional steam and secondary reforming operations. The metals of Group VIII of the Periodic System and/or oxides thereof and metals of the lefthand elements of Group VI and/or oxides thereof are known reforming catalysts. Specific examples of reforming catalysts that can be used are nickel, nickel oxide, cobalt oxide, chromia, molybdenum oxide and rhodium based catalyst on an α-alumina support. The catalyst can be employed with promoters and can also have been subject to various special treatments known in the art for enhancing its properties. Promoted nickel oxide catalysts are generally preferred, and the primary reformer channels are packed with solid catalyst granules, usually comprising nickel or other catalytic agents deposited on a suitable inert carrier material. The catalyst may comprise discrete particles usually in a size range of from 2 to 15 mm in diameter. The particles may have any shape, but they will typically comprise spheres or cylinders. The secondary reforming zone commonly contains a bed of similar catalyst material.

As an alternate to a particulate catalyst, the catalyst may also be coated on the surface of the plates in the various reforming zones. It may be particularly advantageous to coat the primary reforming catalyst onto the plates to provide an upper catalytic section and a lower catalyst-free section that is maintained in heat relationship across the channel defining plates with a catalytic secondary reforming section.

Those skilled in the art understand that the invention can be practiced for the refining of hydrocarbons as part of overall processing techniques and know the appropriate feedstocks for a variety of industrial applications, i.e. as in the production of hydrogen, methanol, ammonia or of (oxo) syngas. Suitable feedstocks for synthesis gas production include relatively impure methane streams having normally up to 20 mol % of $C_2$ hydrocarbons. The fluid hydrocarbon feed of the invention can also include various normally gaseous hydrocarbons other than natural gas or methane such as propane and butane, as well as prevaporized normally liquid hydrocarbons such as hexane or low-boiling fractions such as naphtha.

Figure 2:
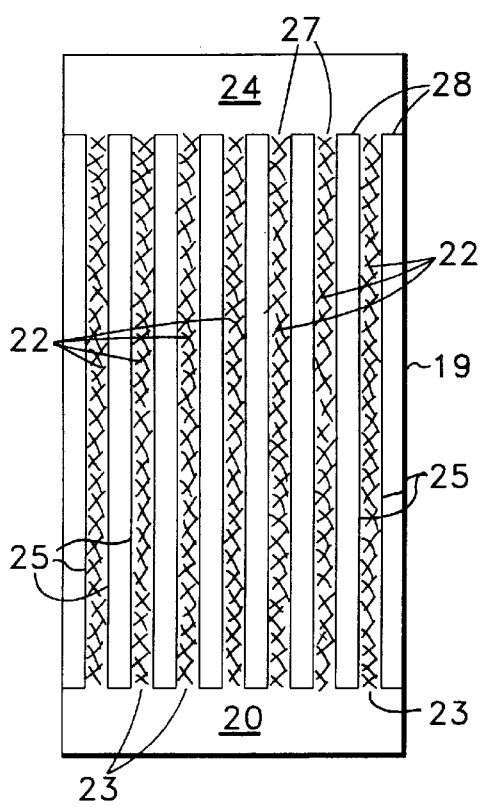
FIG. 2 is a section of the schematic heat exchange reactor shown in FIG. 1 at section 2—2.

Looking then at FIG. 1, in a basic flow arrangement of this invention, a synthesis gas feed comprising natural gas and steam in a steam to methane proportion of from 1.5 to 4 enters the process via line 10 and undergoes heat exchange in a conventional heat exchanger 12 with a synthesis gas product stream carried by a line 14. The preheated feedstream passes via line 16 to a distribution header 18. Distribution header 18 supplies the heated feed to distribution spaces 20 in a heat exchange reactor 19. As further shown by section 2—2 of FIG. 2, distribution space 20 distributes the heated synthesis gas to a plurality of primary reforming reaction channels 22 that retain a reforming catalyst therein. The bottoms 23 of the reactant channels 22 are open to gas flow, but have an appropriate screen material located thereacross to prevent catalyst from falling from channels 22. The heated reforming reactants pass through the channels 22. Collection space 24 collects the effluent from the primary reforming zone across the open tops 27 of channels 22. As shown in FIG. 1 a manifold 26 collects the primary reforming effluent from collection spaces 24 and transfers the effluent via a line 28 into a secondary reforming zone 30. A portion of the primary reforming effluent may be directly diverted to the product line 14 via by-pass stream 32.

Secondary reforming reaction zone 30 is arranged in a traditional manner and contains a as fixed bed of particulate catalyst for promoting the oxidation of remaining methane as well as the reaction of carbon monoxide and hydrogen as further desired. A line 34 transfers oxygen-containing gas into the secondary reaction zone 30. A portion of the natural gas feed may bypass the primary reaction zone 19 via line 33 and directly enter secondary reforming zone 30. Line 34 may also provide additional fuel to the secondary reaction zone as required.

Figure 3:
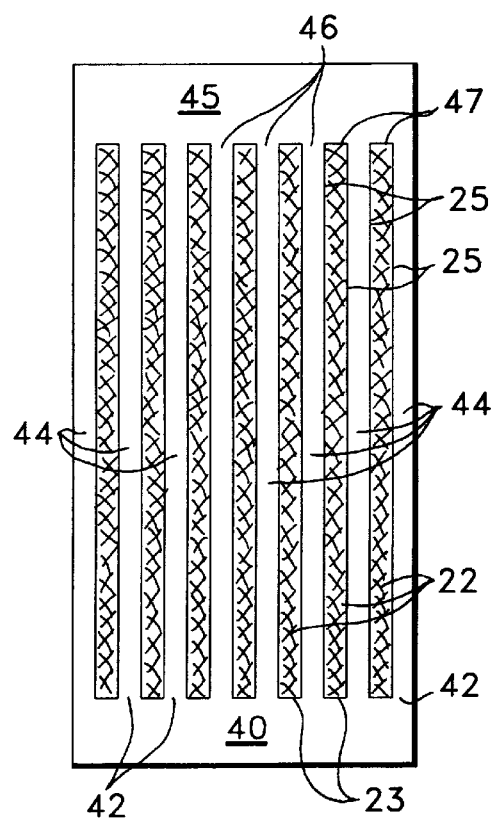
FIG. 3 is a section of the schematic heat exchange reactor shown in FIG. 1 taken at section 3—3.

A line 36 withdraws the heated secondary reforming effluent and passes it to a distribution manifold 38 that distributes the hot gases to distribution spaces 40. As further shown by FIG. 3 which depicts section 3—3 of FIG. 1, distribution spaces 40 distribute the hot gas to inlets 42 of heat exchange channels 44. As opposed to distribution space 20, distribution space 40 has the bottoms 23 of reactant channels 22 closed to gas and catalyst flow to prevent the flow of secondary reforming effluent therein. As the hot gases pass upwardly through heat exchange channels 44, the large surface area provided by the plates 25 that define the heat exchange channels efficiently transfer heat into the reactant channels 22. Collection space 45 collects the cooled secondary reforming gas from the open outlets 46 of heat exchange channels 44. As shown again in FIG. 1, a manifold 48 gathers the collected secondary reforming effluent and transfers it into product line 14 for recovery downstream of exchanger 12 via line 50.

Figure 4:
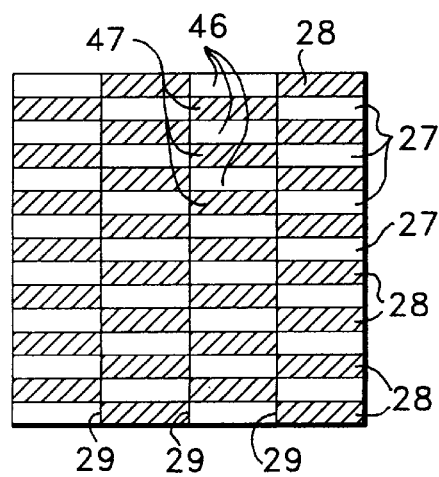
FIG. 4 is a horizontal section of the schematic heat exchange reactor shown in FIG. 1 taken at section 4—4.

The arrangement of collection spaces 24 and 45 to selectively collect the primary reforming effluent and the secondary reforming effluent is more fully appreciated from FIG. 4. As shown by FIG. 4, those portions of reaction channels 22 that coincide with collection space 24 maintain outlets 27 open for free communication therewith. Conversely, those portions of heat exchange channels 28 that coincide with collection space 24 have a closure 28 that prevents fluid communication with collection space 24. Collection space 45 has the reverse relationship to channels 22 and 44 wherein coinciding portions of channels 44 communicate openly across outlet 46 while coinciding portions of channels 22 are blocked from communication with collection space 45 by closures 47. Distribution spaces 20 and 40 have a similar arrangement for establishing and restricting fluid communication with the desired channels. FIG. 4 also shows the partitions 29 that internally segregate collection spaces 24 from collection spaces 45.

Figure 5:
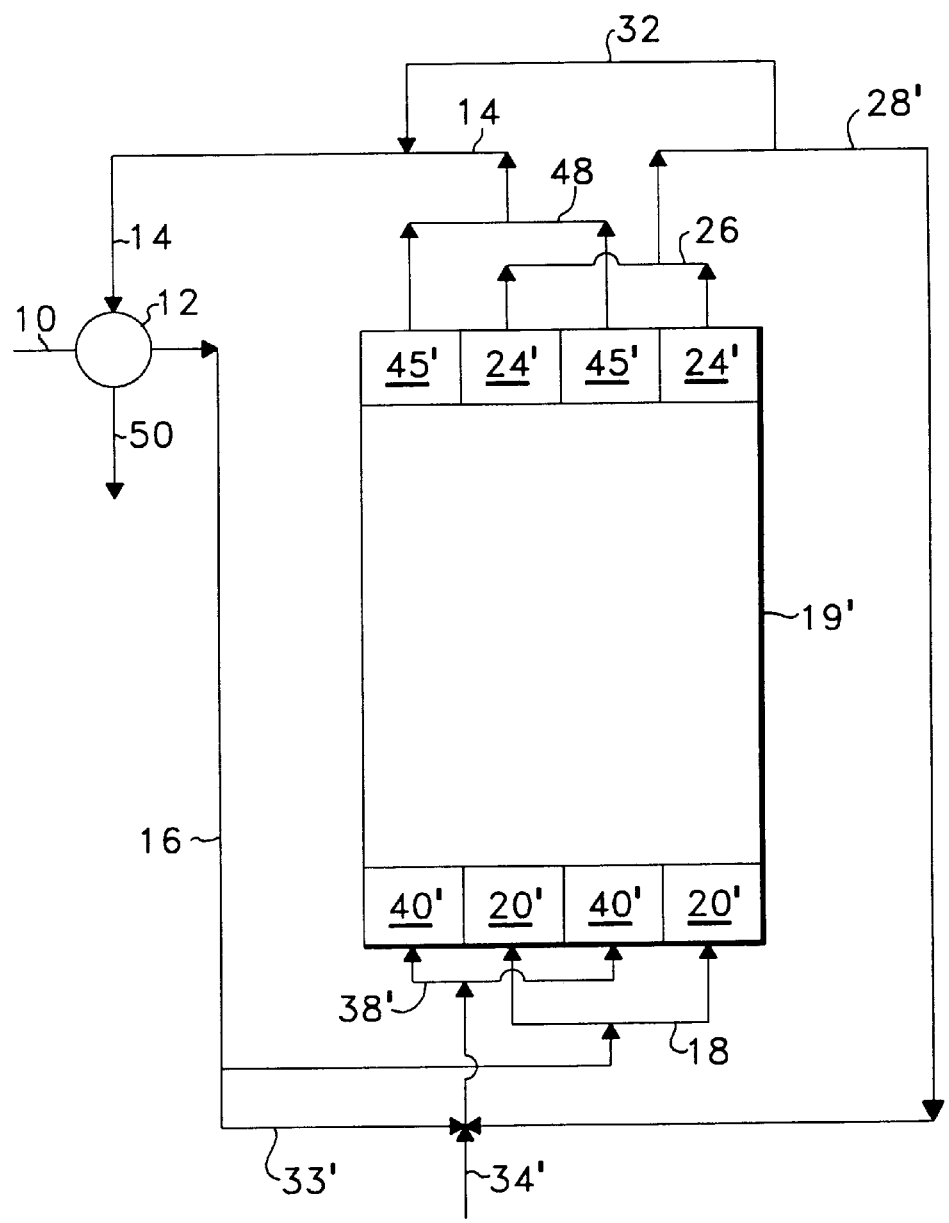
FIG. 5 is a schematic diagram of an alternate arrangement for primary and secondary reforming reaction zones arranged in accordance with this invention.

An alternate arrangement of this invention will integrate the secondary reforming zone with the primary reforming zone in the heat exchange reactor. FIG. 5 shows such an arrangement in simple form where the primary difference between FIGS. 1 and 5 is the elimination of a separate secondary reforming zone 30. The process operates in a very similar manner to that described in conjunction with FIG. 1 and identical reference numbers are employed where the reactor flow stream is substantially the same. Reactor 19' in FIG. 5 differs from reactor 19 by the inclusion of secondary reforming catalyst in the heat exchange channels (not shown). In accordance with FIG. 5, the reforming feed including steam and hydrocarbons is heat exchanged in heat exchanger 12 against the exiting effluent stream 14 to produce a preheated, primary reforming feed carried by line 16 to header 18 for distribution to distribution spaces 20' and for collection of a primary reforming effluent by collection spaces 24' for combining in a collection manifold 26. A line 28' returns the primary reforming effluent, minus any by-passing of effluent through the line 32 to line 14, to a distribution manifold 38'. Feed may also bypass the primary reforming zone and enter the secondary reforming channels directly via line 33'.

Oxygen-containing gas and any additional fuel enters line 28' via feed line 34' for mixture with the primary reforming effluent prior to its distribution by distribution spaces 40'. Some initial reaction of the primary reforming effluent may take place in manifold 38' and distribution space 40'. Combining $O_2$ with the feedstream or the primary reactor effluent must be done in a manner to avoid the presence of oxygen and other combustibles in general or localized proportions that fall within potential explosive ranges. Precautions may include the use of mixing elements as well as specialized header design to maintain safe proportions of the mixtures.

Suitable header designs may include packing or other volume displacement material to minimize the volume of oxygen and fuel mixtures upstream of the secondary reforming reaction.

The principal secondary reforming reaction will take place in contact with the catalyst contained in the heat exchange channels. Contact with a suitable secondary reforming catalyst in the heat exchange channels directly produces heat for indirect heating of the reactants in the primary reforming zone contained within the reactant channels. Collection spaces 45' collect the secondary reforming effluent for withdrawal via line 14 through manifold 48. The synthesis gas product from the reforming process again leaves exchanger 12 through line 50.

Except for the addition of catalyst to the heat exchange channels, the plates and channels defined thereby are the same in reactors 19 and 19'. Suitable plates for this invention will comprise any plates that allow a high heat transfer rate. Thin plates are preferred and usually have a thickness of from 1 to 2 mm. The plates are typically composed of ferrous or non-ferrous alloys such as stainless steel. Preferred alloys for the plates will withstand extreme temperatures and contain high proportions of nickel and chrome. The plates may be formed into curves or other configurations, but flat plates are generally preferred for stacking purposes. Again each plate may be smooth and additional elements such as spacers of punched tabs may provide fluid turbulence in the channels. Preferably each plate has corrugations that are inclined to the flow of reactants and heat exchange fluid.

Figure 6:
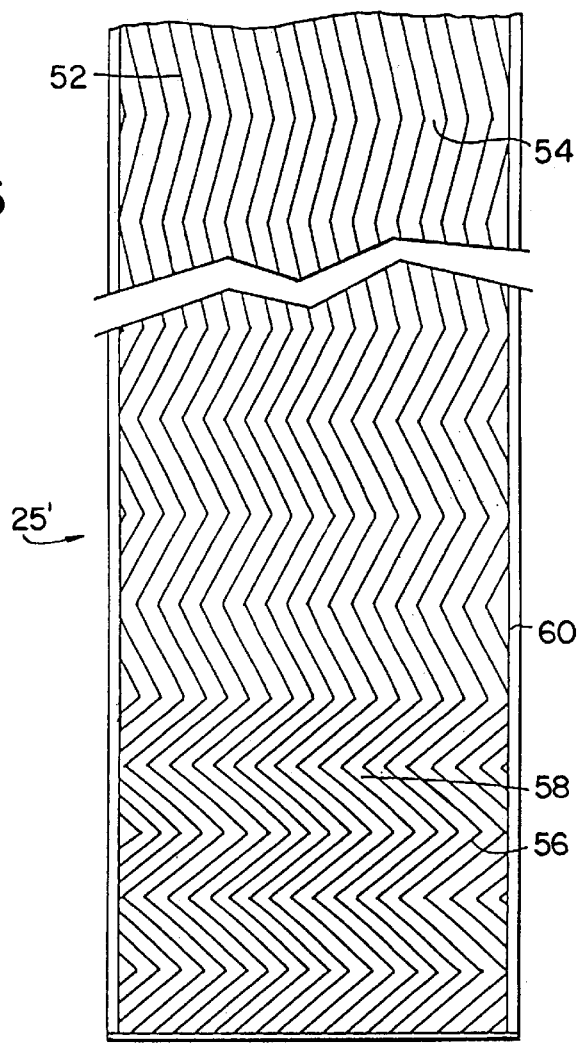
FIG. 6 is a schematic drawing of a flat plate element showing a corrugation pattern.

FIG. 6 shows the preferred corrugation arrangement where the plates 25 that divide the central portion of heat exchange reactor 19 into heat exchange channels and reaction channels are formed by plates 25' having a corrugation arrangement as shown in FIG. 6. The corrugation pattern can serve at least two functions. One function is to structurally support adjacent plates. The other function is to promote turbulence for enhancing heat exchange efficiency in the narrow reaction channel. FIG. 6 shows corrugations defined by ridges 52 and valleys 54. The frequency or pitch of the corrugations may be varied as desired to promote any varying degree of turbulence. Therefore, more shallow corrugations as shown by ridges 52 and valleys 54 will produce less turbulence. Whereas greater corrugation pitches, as shown by ridges 56 and valleys 58, may provide increased turbulence where desired, the pitch of the corrugations and the frequency may also be varied over a single heat exchange channel to vary the heat transfer factor in different portions of the channel. Preferably, the channels may contain a flat portion 60 about their periphery to facilitate closure of the channels about the sides and tops where desired.

Figure 7:
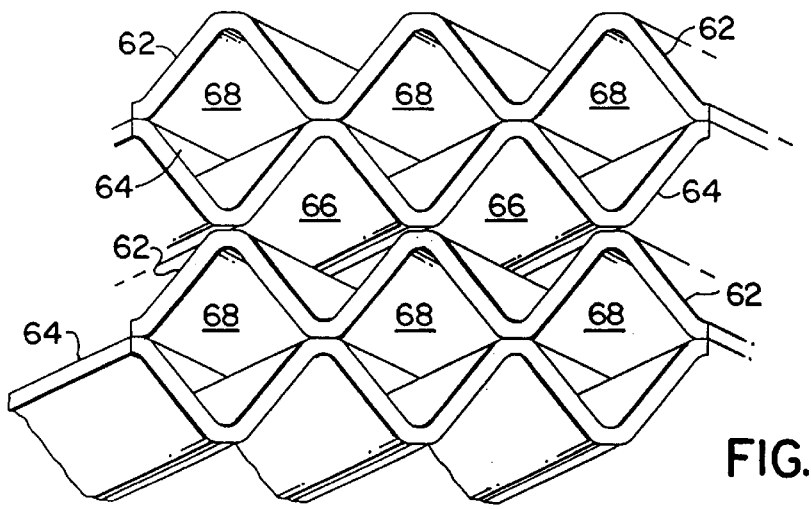
FIG. 7 is an isometric view of corrugated plates forming flow channels.

FIG. 7 shows a typical cross-section of a corrugated plate arrangement wherein the corrugations of plates 62 extend in an opposite direction to the corrugations of plates 64 thereby defining alternate reaction channels 66 and heat exchange channels 68. FIG. 7 illustrates the preferred arrangement of corrugated plates where the herring bone pattern on the faces of opposing corrugated plates extends in opposite directions and the opposing plate faces contact each other to form the flow channels and provide structural support to the plate sections.

In general, the invention relies on relatively narrow channels to provide the efficient heat exchange across the plates. The corrugations maintain a varied channel width defined by the height of the corrugations. In general, the channel width should be less than one inch on average with an average width of less than 1/2 inch preferred. In the case of corrugations, the average channel width is most practically defined as the volume of the channels per the cross-sectional area parallel to the primary plane of the plates. By this definition corrugated plates with essentially straight sloping side walls will have an average width that equals half of the maximum width across the channels.

The reaction zones for the process of this invention may indirectly contact the reactants with the heat exchange fluid in any relative direction. Thus, the flow channels and inlets and outlets of the reaction zones may be designed for cocurrent, countercurrent, or cross-flow of reactant fluid relative to the heat exchange fluid. Preferred process arrangements for practicing this invention will pass reactants in cocurrent flow or countercurrent flow to maximize contact with the heat exchange fluid and the heat producing reaction zone. Cross-flow of reactants is generally preferred to minimize the pressure drop associated with the flow of reactants through the reactor. For this reason, a cross-flow arrangement can be used to provide the reactants with a shorter flow path across the reaction zone.

The shorter flow path reduces overall pressure drop of the reactants as they pass through catalyst particles retained in the reactor. Lower pressure drops can have a two-fold advantage in the processing of many reactant streams. Increased flow resistance, i.e., pressure drop, can raise the overall operating pressure of a process. In many cases, product yield or selectivity is favored by lower operating pressure so that minimizing pressure drop will also provide a greater yield of desired products.

It is also not necessary to the practice of this invention that each reactant channel be alternated with a heat exchange channel. Possible configurations of the reaction section may place two or more heat exchange channels between each reactant channel to reduce the pressure drop on the heat exchange medium side. When used for this purpose, a plate separating adjacent heat exchange channels may contain perforations.

Additional channels defined by the plates can provide a variety of supplementary functions. In addition to channels for the primary and secondary reforming reactions, other channel functions may include preheating feed to the primary reaction zone, cooling the effluent from the secondary reforming zone, indirectly heating the primary reformer channels with a gas stream as shown in FIG. 1, and further heating the preheated feed by indirect heat exchange with the secondary reforming zone.

Figure 9:
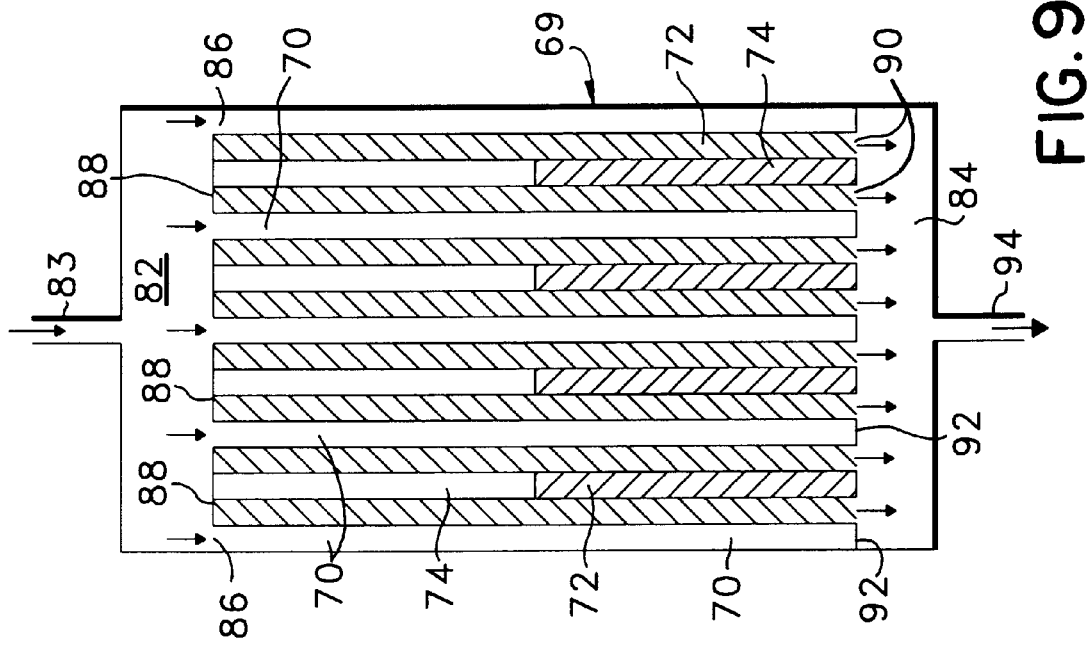
FIGS. 8 and 9 are schematic diagrams illustrating an alternate flow arrangement for heat exchange channels in a heat exchange reforming reactor of this invention.
Figure 8:
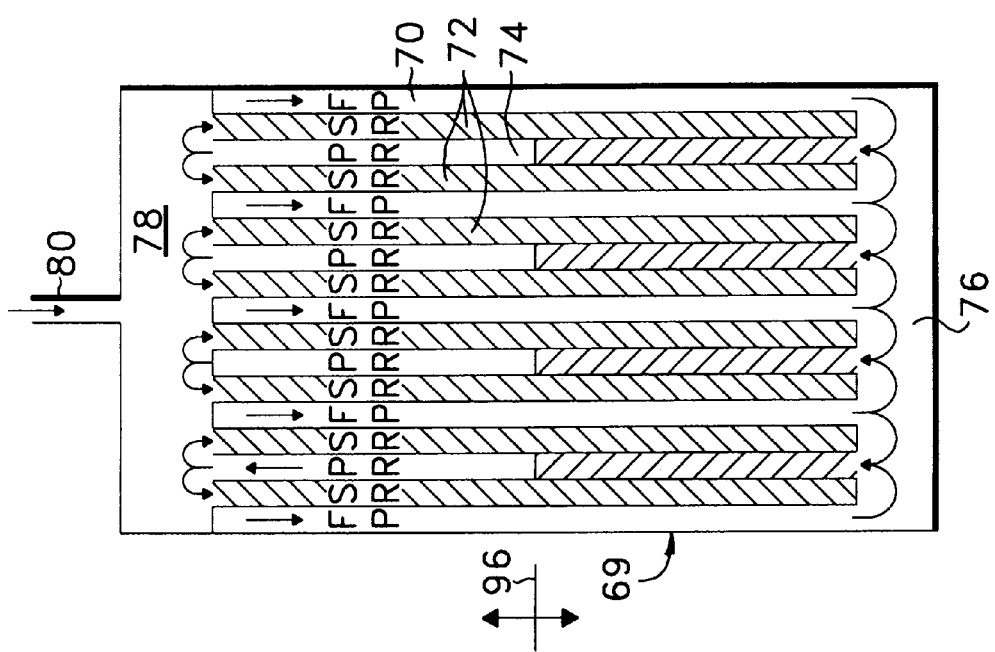

A reactor arrangement 69 having multi-function channels is shown in FIGS. 8 and 9. FIG. 8 shows one such channel arrangement with the functions of the different channels coded in the schematic representation. The letters "FP" stand for a feed preheat channel. The letters "SR" indicate a secondary reforming channel and the letters "PR" represent a primary reforming channel. As shown by FIG. 8, fluid flow through the channels in the desired manner requires two different collection and distribution space arrangements. Fluid flow through the distribution/collection spaces can be controlled in a manner analogous to that described and depicted through FIGS. 1–4. Looking then at FIG. 8, feed to the primary reforming zone passes through the feed preheat channels 70 where indirect heat exchange with the secondary reforming channels 72 raises the temperature of the feed to that desired for initial reaction in the primary reforming channel 74. Preheated feed from channels 70 flows into a manifold space 76. Manifold space 76 communicates the preheated feed with the primary reforming channels 74. The preheated feed passes upwardly through the primary reforming channel 74 and into another manifold space 78. An oxygen-containing gas and optionally additional feed or combustion fuel may enter manifold space 78 through a nozzle 80. Manifold space 78 mixes any fluid entering via nozzle 80 with the primary reforming zone effluent and distributes the mixture as feed to the secondary reforming channels 72. The secondary reforming channels 72 preferably contain a secondary reforming catalyst over their entire length that promotes the exothermic secondary reforming reaction. As the mixture passes downwardly through secondary reforming channels 72, it heats the channels 74 containing the primary reactants as well as the feed preheat channels 70.

FIG. 9 shows an additional distribution space 82 and collection space 84 that form a part of reactor 69 and are separated from collection spaces 78 and 76 with partitions similar to U partitions 29 shown in FIG. 1. Feed enters the reactor 69 via a nozzle 84. Distribution space 82 distributes the primary reforming zone feed to preheat channel 70 across open inlets 86. Closure plates 88 block the tops of primary reforming channels 74 and secondary reforming channels 72 where the channels are contiguous with the distribution space 82. Once distributed to the feed channels, the primary reforming feed continues to flow through the reactor 69 as described in conjunction with FIG. 8. The secondary reforming effluent leaves reactor 69 through a collection space 84 that communicates across the open bottoms 90 of secondary reforming channels 72. Outlets 90 contain an appropriate screen material to retain catalyst in the secondary reforming channels while permitting fluid to exit from the channels. The bottoms of primary reforming channels 74 are closed by closure plates 92 wherever they pass across collection space 84. A secondary reforming nozzle 94 withdraws the collected secondary reforming effluent. Any by-passing of feed between the primary and secondary reforming zone may be accomplished by external piping that communicates any of distribution space 82, collection space 84, and manifold spaces 76.

Additional preheating as well as isolation of the exothermic reaction zones from direct alignment with the endothermic reaction zones is readily accomplished by varying the location of the catalyst loading between channels. Optionally, the space at the one end of a channel may be used as a feed preheating zone or as an effluent cooling zone. FIGS. 8 and 9 schematically illustrate a partial loading of catalyst in the channels by a catalyst level line 96. Primary reforming channels 74 may contain catalyst from below line 96 to the inlets of the channels 74. In such an arrangement, as feed flows downwardly through feed preheat channels 70, the secondary reforming zone initially heats the feed indirectly with the reaction section of the secondary reforming channels 72. The primary reforming feed after heat exchange enters the primary reforming channel for reaction therein. Heat from the reaction in the secondary reforming channel 72 heats the primary reforming reaction zone in a lower portion of channel 74 as the feed passes upwardly therethrough. The effluent from the primary reaction zone continues to receive heat from the upper portion of channels 72 until it exits channels 74 and enters the tops of secondary reforming zone channels 72 for contact with the catalyst contained therein.

A variety of other combinations of channel functions can be combined in single pass or multiple pass arrangements. The use of a plate heat exchange reactor facilitates arrangement of heat exchange channels in a wide degree of desired functionality in either single or multiple stack arrangements. For example, the upper and lower sections of channels 74, shown as theoretically separated across catalyst loading line 96, may be readily separated physically into two separate reaction zones. Collection and distribution manifolds similar to those shown in FIGS. 1–4 and 8 and 9 can be used to internally communicate fluid streams between the sections of separated channels. More usefully, the manifold arrangements may be used to externally communicate reaction channels contained in a single reaction vessel. External communication will facilitate control of gas streams to the different reaction zones and heat exchange zones. External control will also permit a wide variety of flow paths to be provided between the different channel arrangements.

Figure 11:
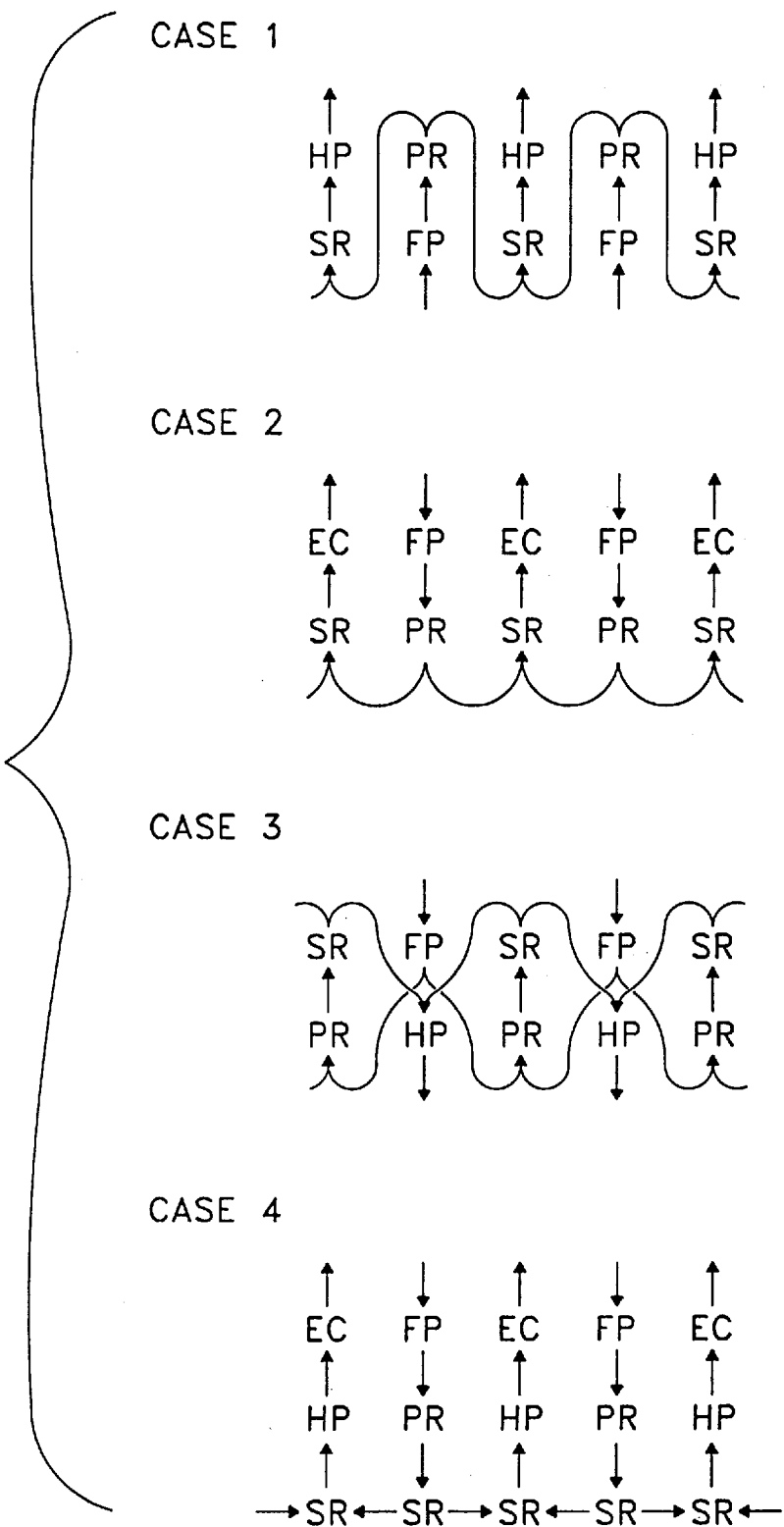

In the way of further illustration, FIGS. 10 and 11 are charts showing a coding for possible arrangements of channel functions across a plurality of channels defined by plate elements. The codes FP, SR, and PR were previously explained. Additional codes used in charts 10 and 11 include "EC" that stands for effluent cooling and "HP" that refers to a zone that contains the hot gas stream from the secondary reforming reaction channels that heat the primary reforming reaction channels.

FIG. 10 depicts three cases of configurations for interconnecting parallel channels in a repeating pattern of functions. Case 1 of FIG. 10 represents the arrangement of channels depicted in FIGS. 8–9 where a secondary reforming channel separates the feed preheat and primary reforming channels so that there is one primary reforming channel for every six channels overall. Case 2 represents an arrangement that cools the effluent from the secondary reforming channels against the incoming feed and provides one primary reforming channel for every 3 channels overall. Case 3 is another channel arrangement that provides one primary reforming channel and two secondary reforming channels for every 6 channels.

FIG. 11 represents further arrangements wherein multiple reaction stacks provide dual banks of channels which can be interconnected externally or internally in a manner that provides a plethora of different channel functions. All of the configurations in the chart of FIG. 11 are simplified representations of upper and lower-two pass heat exchange arrangements with different functions described by the previously described codes and an additional code "HP" that represents a channel used to indirectly heat the primary reforming zone.

Case 1 of FIG. 11 shows a two-pass exchanger section. In the lower channel bank the primary reforming feed undergoes indirect heat exchange with the plates that contain the secondary reforming reaction on their opposite sides. The upper channel banks react the preheated feed in the primary reforming zone opposite channels that contain the hot effluent from the secondary reforming zone and that heat the primary reforming zone. Externally connected manifolding transfers the effluent from the primary reforming reaction zone to the secondary reforming reaction zone.

Case 2 of FIG. 11 representatively illustrates another two stack channel arrangement. The upper channel section cools the product stream from the secondary reforming zone by indirect heat exchange opposite the entering feedstream. Functionally the upper section serves essentially the same purpose as exchanger 12 in FIGS. 1 and 5. The lower channel section provides indirect heating from the secondary reforming zone directly across from the primary reforming zone.

Case 3 of FIG. 11 is yet another variation on a flow scheme that uses manifolds between two banks of heat exchange channels to establish a heat exchange arrangement similar to that shown in case 1 of FIG. 11. Case 3 differs from Case 1 by directing fluids in a countercurrent manner as opposed to the cocurrent fluid flow direction of Case 1.

Finally, case 4 shows an arrangement wherein two separate banks of heat exchange channels are used in connection with a secondary reforming zone. The secondary reforming zone may be integral with the channels or may be located externally to the channel banks. The secondary reforming zone may also serve as a connecting manifold for communicating channels. In this arrangement the feed enters the feed preheating zone, and after exchange against the effluent from the secondary reforming zone, the feed enters the primary reforming zone. Hot gases from the secondary reforming reaction pass directly opposite to, and provide heat to, the primary reforming zone by indirect heat exchange. The effluent from the primary reforming zone enters the secondary reforming zone which may be arranged as channels or as a fixed bed of secondary reforming catalyst. The effluent from the secondary reforming zone supplies hot gases to heat the primary reforming zone which then undergoes further indirect cooling with the incoming primary reforming feed.

Further enhancement of temperature control may be obtained by using intermediate injection of the oxidation fluid or additional fuel. Operating with a countercurrent or cocurrent flow of the primary reactants leaves the sides of the channels available for cross flow injection of intermediate oxidation fluid of feed. A cross flow pattern provides additional control on the generation of heat at specific locations thereby allowing adjustment of the temperature profile in the secondary reforming zone. Where the secondary reforming zone exchanges heat directly against the primary reforming zone, intermediate injection can also be used to influence the temperature profile within the primary reforming zone.

Figure 12:
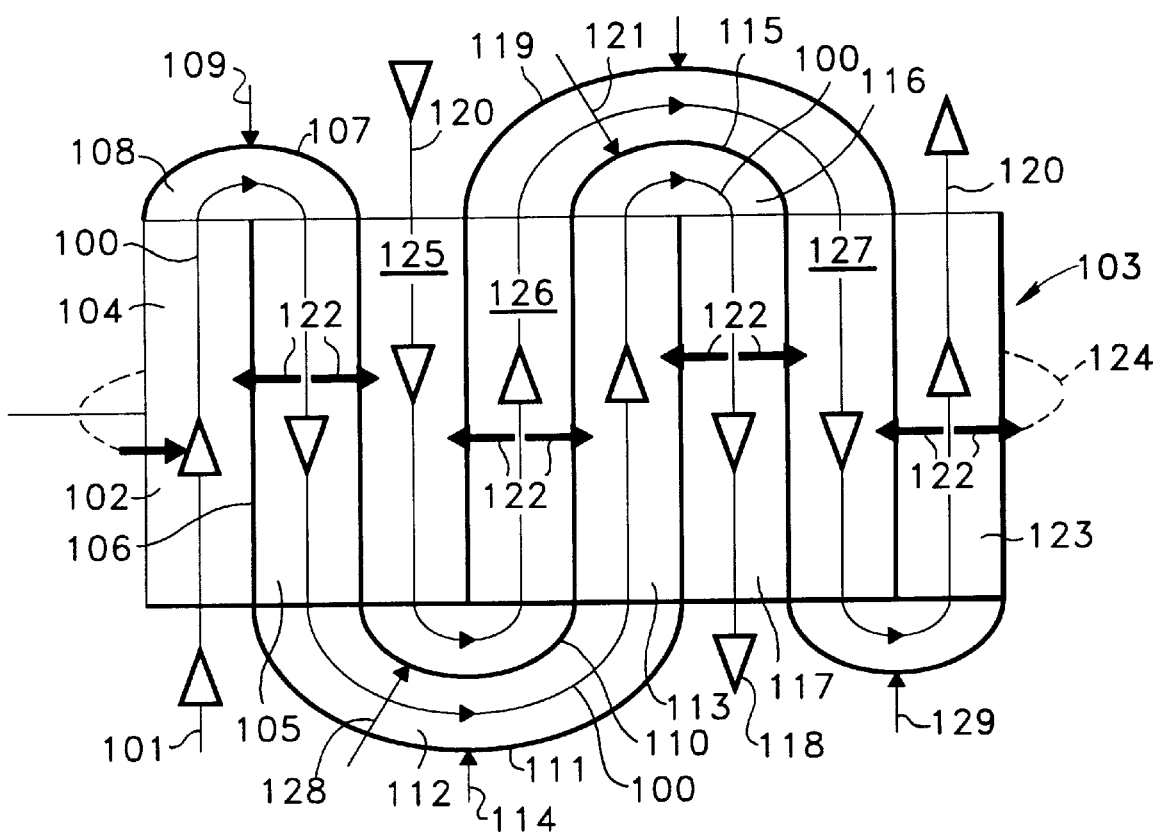
FIGS. 12 and 13 show conceptual arrangements of reactors having multiple independent channel path arrangements.
Figure 13:
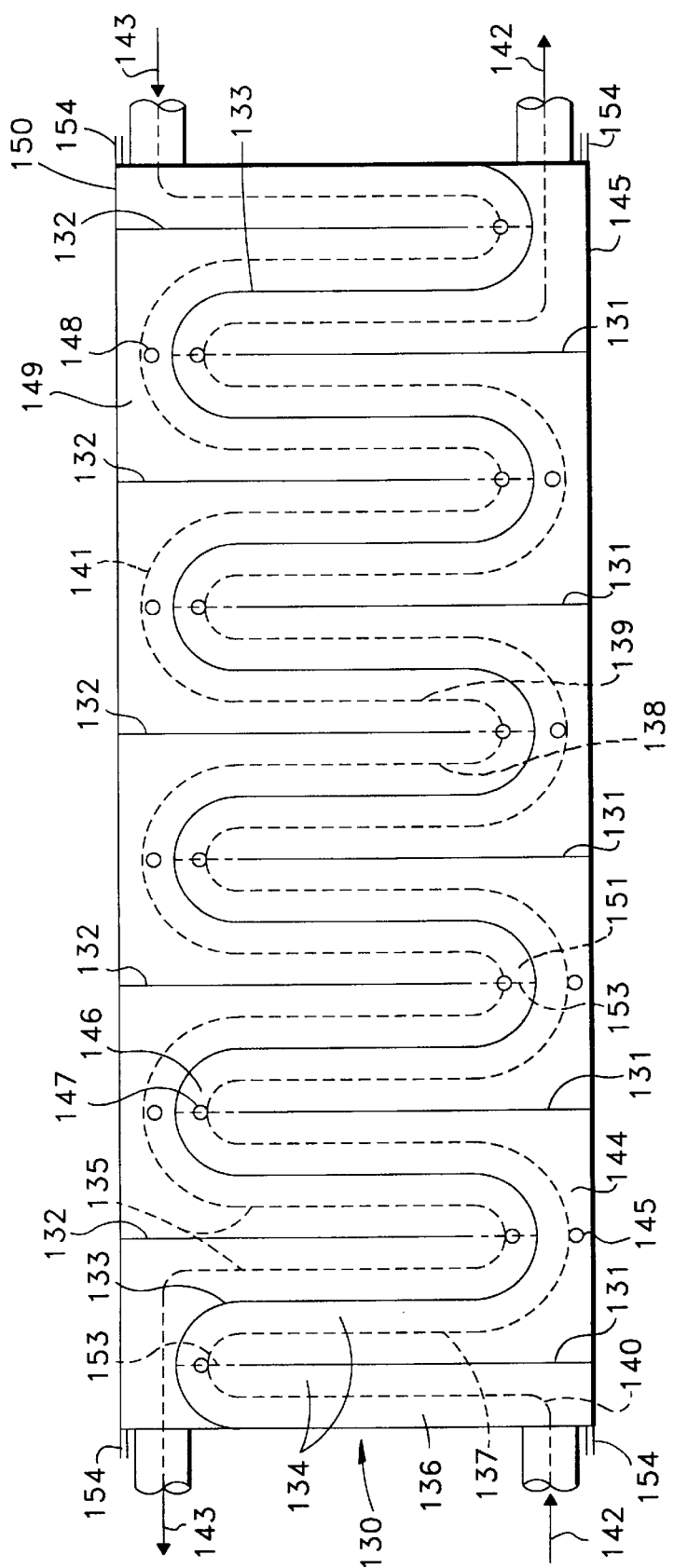

Another form of this invention provides two continuous channel flow paths that can pass two fluids independently through multiple channel passes in a heat exchange reactor arrangement. The arrangement can segregate streams for parallel movement of reactants and/or heat exchange fluids in a heat exchange relationship. FIGS. 12 and 13 show conceptual arrangements of reactors having multiple independent channel path arrangements that combine endothermic and exothermic reaction steps on the same reactant stream. Useful processes that can use such an arrangement include steam reforming, as previously described, and the production of styrene by the dehydrogenation of ethylbenzene.

Looking at the production of styrene, FIG. 12 shows an ethylbenzene feed represented by arrow 101 entering a first segregated channel path 102 of a reactor arrangement 103 having dual independent channel passes that conducts the one flow along a first flow path 100. As the feed passes along flow path 100, it first contacts a dehydrogenation catalyst in a dehydrogenation channel 104. Heat from a combustion channel 105 passes across a heat transfer plate 106 to promote the endothermic dehydrogenation reaction in channel 104. A folded plate 107 defines the disparate boundaries of reaction channel 102 and heating channel 105. "U" shaped plate 106 provides a common boundary between reaction channel 102 and heating channel 105. A curved upper part of plate 107 defines a manifold space 108 for passing a mixture of ethylbenzene, styrene, and hydrogen generated from the dehydrogenation reaction to heating channel 105. Air also enters manifold space 108 as indicated by arrow 109 for the promotion of hydrogen combustion in channel 105. Both channels 102 and 105 will typically contain a catalyst material for the dehydrogenation of styrene and the combustion of hydrogen, respectively. The hydrogen combustion catalyst will preferably have a low selectivity for the combustion of ethylbenzene and styrene. Another curved section 110 of plate 107 and a curved section 111 of "U" shaped plate 106 define the inner and outer boundaries, respectively, of an additional manifold space 112 that transfers unreacted ethylbenzene and styrene to a second reaction channel 1 13 for the dehydrogenation of additional ethylbenzene. Manifold space 112 may add additional air in the direction of arrow 114, if desired. Again, a curved section 115 of plate 107 defines an inner manifold space 116 that transfers a mixture of air, ethylbenzene, styrene, and hydrogen to a second heating channel 117 that contains a catalyst for the selective combustion of hydrogen. Additional air may enter inner manifold space 116 in the direction of arrow 121. A product stream containing styrene exits the second heat exchange channel 117 in the direction of arrow 118.

Folded plate 107 in combination with an additional U-shaped plate 119 defines two additional pairs of reaction channels and heating channels along a flow path 120. The heating channels and reaction channels contain dehydrogenation and selective hydrogen combustion channels as previously described for the channels along flow path 100. The channels along flow path 120 also have a similar arrangement of manifolds and air mixing spaces to those described for the channels along flow path 100. Accordingly, along the length of flow path 120, reactants pass through a reaction channel 125, a heating channel 126, a second reaction channel 127, and a heating channel 123. Styrene products are collected and combined from the outlets of the final heating channels along the flow paths 100 and 120.

As combustion of hydrogen takes place in the heating channels, it provides direct heating of the reactants for the next step of ethylbenzene dehydrogenation in the downstream reaction channel as well as indirect heating of the adjacent reaction channels across the common plate boundaries in the directions indicated by arrows 122. Dual path heat exchange channel arrangement 103 may also have means for conducting heat from an end heating channel 123 to reaction channel 102 along a path indicated by line 124.

FIG. 12 shows only one form of construction for the multiple independent channel pass arrangement of this invention. The undulation of folded plate 107 may be extended to provide parallel or series flow trains of additional reaction passes. The number of independent channel passes provided by the addition of U-shaped plates along the folds of plate 107 are unlimited. Preferably, the reactor configuration uses a single folded plate as the primary channel defining element; however, multiple folded plates can be used.

Reactors providing the multiple independent passes of reaction and heating channels may have various configurations. FIG. 13 shows another way of constructing the multiple independent flow paths for the channel reactor arrangement. The reactor 130 provides the dual flow path channel arrangement through a series of lower separation plates 131, upper separation plates 132, and a continuous serpentine plate 133. Preferably, plates 131 and 132 divide the alternating semi-oval areas 134 and 135 into alternating pairs of upflow and downflow channels. Separation plate 131 defines upflow and downflow channel pairs 136 and 137 while upper separation plates 132 defines upflow and downflow channel pairs 138 and 139. The upflow or downflow direction in each individual channel depends on the direction in which fluid circulates through the separate channel paths 140 and 141. The overall flow direction of a first stream, as indicated by arrows 142, and a second stream, as indicated by arrows 143, may run in a cocurrent or countercurrent direction.

Outer manifold spaces 144 defined by the lower separation plates and a bottom plate 145 may each contain an injection pipe 145 for the introduction of fluids at intermediate points along the flow path length. Similarly, an inner manifold space 146 above the channels divided by the lower separation plates 131 may contain a injection pipe 147 for the injection of fluids at intermediate points along the flow path 140. The upper flow path 141 may also have injection points 148 at outer manifold spaces 149 defined by the upper separation plates 132 and their retaining plate 150. Inner manifold spaces located below the channels defined by upper separation plates 132 may also contain a pipe injector 151 for adding fluids at an intermediate point along flow path 141.

Reactor arrangement 130 may contain any form of catalyst in channel pairs 136 and 137 and channel pairs 138 and 139. Typical types of catalyst will include particulate material retained within the channels by appropriate screen devices or coatings applied to the surface of the plates in the channel sections. The arrangement of reactor 130 provides particular benefits when used with coated catalyst plates. For example the plates may be easily recoated. In the case of coated catalyst, the arrangement of reactor 130 may permit removal of the upper separation plates and lower separation plates from the rest of the reactor body. Flanges 154 may be provided on the sides of the reactor for this purpose. Separating the flanges 154 permits the removal of the separation plates 131 and 132. A catalyst coating previously applied to these plates may now be washed off from the plates for reapplication of fresh catalyst material. The overall construction of the plates allows them simply to be dipped for removal and reapplication of a suitable catalyst material. Although not as convenient, separate catalyst coatings may be applied to each side of the plates 132 and 131. A greater accessibility permitted by the removal of the upper and lower separation plates will also permit increased access to the area between the semi-oval volumes defined by serpentine plate 133. Ready removal of the plates 131 and 133 is possible by leaving a small amount of clearance at the lateral end of each plate. In view of the open communication of the channels at the ends of plates 131 and 132, small clearances at the sides of the plate will not interfere unduly with the operation of the reactor while facilitating ready assembly and disassembly for the maintenance of the catalytic material contained therein.

Lower separation plates 131 and upper separation plates 132 may contact the curved bottoms of serpentine plate 133 with perforated plate section 152 and 153, respectively, to stabilize the separation plates. The perforations will permit fluid transfer across the separation plates at the top or the bottoms of the channels. The perforation sections may also have advantages in facilitating loading of different catalysts into the channels defined by the common plate elements.

EXAMPLES

The effect of using the process and reactor arrangement of this invention to conserve reactant products and allow greater control of the synthesis gas composition by reducing the heating requirement was investigated in a simulation of a steam reforming process for the production of synthesis gas.

Example 1

In this example, 100 g mole of a methane feed is combined with 2.5 to 3.0 times g moles of steam for the production of a methanol synthesis feed and is split between a primary reforming reaction zone and secondary reforming reaction zone in a proportion to achieve a target bimolecular hydrogen to carbon ratio of 2:1 in the effluent and to supply all of the necessary heat input to the primary reforming reaction zone from the secondary reforming reaction zone. The primary reforming reaction zone receives 46.4 g moles of the feed and operates at an average temperature of about 800 to 870° C. and a pressure of 3.8 MPa. The primary feed contacts a nickel type catalyst at a GHSV of 5000–8000 h$^{-1}$. Another 53.6 g moles of the feed passes to a secondary reformer along with 44.6 g moles of oxygen and contacts another nickel based catalyst in the secondary reforming reaction zone at an average temperature of 1065° C. and a pressure of 3.8 MPa. Uniting of the effluents from the two reaction steps results in a combined product stream of 500 g mole having an H$_2$/C ratio of 2.0:1. The overall heat efficiency from this operation is 55% and is representative of the heat efficiency that is normally attainable with tube type heat exchange arrangements.

Example 2

In this example another 100 g of a methane feed along with 250 g moles of steam is again split between a primary reforming reaction zone and secondary reforming reaction zone in a proportion to achieve a target bimolecular hydrogen to carbon ratio of 2:1 in the effluent and to supply all of the necessary heat input to the primary reforming reaction zone from the secondary reforming reaction zone. The primary reforming reaction zone this time receives 60 g moles of the feed and operates at an average temperature of about 800 to 870° C. and a pressure of 3.8 Mpa. The primary feed again contacts a nickel type catalyst at a GHSV of GHSV of 5000–8000 h$^{-1}$. In this case the effluent, in combination with 40 g moles of the methane, passes to a secondary reformer, along with 35 g moles of oxygen, and contacts another nickel based catalyst at an average temperature of 1065° C. and a pressure of 3.8 Mpa. The effluent from the two reaction steps results in a combined product stream of 54.3 g moles having an H/C ratio of 2.21. The overall heat efficiency from this operation is 83% and is readily obtainable with a plate channel arrangement of this invention.

The higher heat efficiency obtainable by the use of the plate heat exchange provides a number of significant benefits. First, the overall product production of H$_2$ was raised from 2.15 to 2.34 moles per mole of methane. The oxygen requirement for the partial oxidation of the secondary reforming step fell by 20 vol. %. Lower oxygen requirements reduces utility expense by requiring less compression for air separation. A 20% decrease in air compression requirements translates into a power savings of as much as 4000 kW for a 2500 ton per day plant. This decrease means a reduction in the steam purge gas requirement for the turbogenerator and a lowering of methane slippage in the synthesis gas production. Reduction of methane in synthesis gas will also result in smaller gas flow in the methanol recycle loop thus reducing capital costs for the methanol reaction as well as the recycle compressor. Thus, there are a number of savings associated with improving the thermal efficiency of the primary/secondary synthesis gas steps.

Example 3

In this example, a computer simulation models the specific operation of a styrene process using the multiple independent channel pass arrangement of this invention as shown in FIG. 12. The simulation uses known kinetic parameters of the dehydrogenation and hydrogen combustion reactions along with experimentally verified heat transfer coefficients across the common boundaries of the reaction and heating channels to provide the results. The kinetic information is based on the activity of an iron oxide type dehydrogenation catalyst and a platinum-alumina type selective hydrogen combustion catalyst.

With respect to the reference numbers in FIG. 12, a mixture of steam and ethylbenzene in a mol ratio of 0.855 and 0.145 passes as feed to reaction channels 102 and 125 in equal portions. Table 1 shows mol fraction composition of the streams passing from reaction channels to heating channels to the remainder of the dual path flow streams. Both of the feedstreams enter reaction channels 102 and 125 at a temperature of about 112° F. and a pressure of about 10.3 psi. As the partially reacted feedstream leaves reaction channel 102 and continues along flow path 100, 44 manifold space 107 receives approximately 20.7% of the total injected air before entering heating channel 105. After further dehydrogenation of the feed in reaction channel 113 approximately 32.9% of the total injected air mixes with the effluent from reaction channel 113, before entering heating channel 117. Along flow path 120, approximately 38.3% and 8.1% of total injected air mix, respectively, with the effluents from reaction channels 125 and 127 as indicated by arrows 128 and 129. Air rates to the different heating channels are varied in order to maximize product yield in view of the different heat transfer rates into and out of the channels as indicated in Table 2. The mixing of the air and the direct and indirect heating of the reactants along the flow paths 100 and 102 maintains a constant temperature of approximately 112° F. in all of the heating and reaction channels. Passage of the reaction streams along the flow paths and through the catalyst imposes a pressure drop that reduces the final effluent pressure from heating channels 117 and 123 to approximately 7.3 psi. The effluents from reaction channels 117 and 123 both have a molar ethylbenzene concentration of approximately 3.3.

What is claimed is:

1. A process for contacting reactants with a catalyst in a reaction zone while indirectly heating the reactants by contact with combustion gases formed in a heat producing zone, the process comprising:

a) contacting a primary reactant stream with a catalyst for the promotion of an endothermic process in a plurality of narrow reaction channels defined by principal spaced apart plates, wherein at least a portion of the principal plates define one or more heat exchange channels on a side opposite one or more reaction channels and a plurality of secondary plates divide the heat exchange channels into oxidation channels and preheat channels;

b) indirectly heating the primary reactant stream in the reaction channels by heat exchange with a hot gas stream across the principal plates that define the reaction channels;

c) collecting a primary effluent stream from the reaction channels, d) passing an oxygen containing stream and at least a portion of the primary effluent stream or a portion of the primary reactant stream to an oxidation zone contained within the oxidation channels to produce a secondary effluent stream;

e) passing at least a portion of the secondary effluent stream through the preheat channels and into contact with the principal spaced apart plates to supply the hot gas stream for indirect heat exchange with the reaction channels as described in step (b); and, f) recovering a product stream comprising at least a portion of the primary effluent stream or the secondary effluent steam.

2. The process of claim 1 wherein the principal plates define alternate reaction channels and heat exchange channels.

3. The process of claim 2 wherein the principal plates define at least two separate flow paths having alternate pairs of reaction channels and heat exchange channels.

4. The process of claim 1 wherein the principal and secondary plates define corrugations and the corrugations maintain the spacing of the principal and secondary plates.

5. The process of claim 1 wherein the catalyst in the reaction channels comprises a particulate material retained in the channels.

6. The process of claim 1 wherein the reaction channels have an average width of less than 1 inch.

7. The process of claim 1 wherein the primary reactant stream comprises ethyl benzene, the catalyst in the reaction channels promotes the dehydrogenation of ethyl benzene to styrene, and the oxidation zone contains a catalyst for the selective combustion of hydrogen from the dehydrogenation reaction.

8. The process of claim 1 wherein the primary reactant stream comprises methane and steam and the catalyst promotes the reforming of methane to synthesis gas.

9. A process for contacting reactants with a catalyst in a reaction zone while indirectly heating the reactants by contact with combustion gases formed in a heat producing zone, said process comprising:

a) contacting a primary reactant stream comprising a methane containing stream and a steam containing stream with steam reforming catalyst in a plurality of narrow reaction channels defined by principal spaced apart plates to conduct a primary reforming reaction;

b) indirectly heating the primary reactant stream in the reaction channels by heat exchange with a hot gas stream across the principal plates that define the reaction channels and that further define one or more heat exchange channels on a side opposite one or more reaction channels, wherein the heat exchange channels are divided by a plurality of secondary plates into oxidation channels and preheat channels, c) collecting a primary effluent stream from the reaction channels;

d) passing an oxygen containing stream and at least a portion of the primary effluent stream or a portion of the methane containing stream to an oxidation zone contained within the oxidation channels to produce a secondary effluent stream;

e) passing at least a portion of the secondary effluent stream through the preheat channels into contact with the principal plates to supply the hot gas stream for indirect heat exchange with the reaction channels as described in step (b); and, f) recovering a synthesis gas comprising at least a portion of the primary effluent stream or the secondary effluent steam.

10. The process of claim 9 wherein a feedstock comprising the methane containing stream and the steam stream passes through a portion of the heat exchange channels that define the preheat channels to indirectly preheat the feedstock across from the oxidation channels with heat from a secondary reforming reaction to produce a preheated feedstock, at least a portion of the preheated feedstock passes through the oxidation channels while indirect heat exchange with the oxidation channels indirectly heats a primary reforming reaction with heat from the secondary reforming reaction to produce a primary reaction effluent, a portion of the primary reaction effluent reacts with an oxygen containing gas in the oxidation channels to produce a secondary reaction effluent and the synthesis gas comprises a portion of the primary effluent and the secondary effluent.

11. The process of claim 9 wherein the ratio of H:C in the synthesis gas is in a range of from about 2.0 to about 2.2.

12. The process of claim 9 wherein the methane containing stream contains at least 10 wt % C2 or higher hydrocarbons and the synthesis gas product has a H:C ratio in a range of from about 2.0 to about 2.2.

13. The process of claim 9 wherein the synthesis gas contain less than 2.5 wt % methane.

14. A process for contacting reactants with a catalyst in a reaction zone while indirectly heating the reactants by contact with combustion gases formed in a heat producing zone, said process comprising:
  a) contacting a feedstock comprising methane and steam with a steam reforming catalyst in a plurality of narrow reaction channels defined by a plurality of principal spaced apart plates;
  b) indirectly heating the feedstock in the reaction channels by heat exchange with a hot gas stream that passes through heat exchange channels defined by the principal plates and interleaved with the reaction channels, the heat exchange channels divided by a plurality of secondary plates into oxidation channels and preheat channels;,
  c) collecting a primary effluent stream from the reaction channels;
  d) passing an oxygen containing stream and at least a portion of the primary effluent stream to an oxidation zone contained within the oxidation channels to produce a secondary effluent stream;
  e) passing at least a portion of the secondary effluent stream through the preheat channels into contact with the plates in the heat exchange channels to indirectly heat the reaction channels as described in step (b); and,
  f) recovering a synthesis gas comprising at least a portion of the secondary effluent stream.

15. An apparatus for contacting reactants with a catalyst in a reaction zone while indirectly heating the reactants by contact with combustion gases formed in a heat producing zone, the apparatus comprising:
  a plurality of alternate reaction channels and heat exchange channels defined by a plurality of primary plates to have a reactant inlet at one end of the reaction channels, a reactant outlet at an opposite end of the reaction channels, a heating fluid inlet at one end of the heat exchange channels, and a heating fluid outlet at the opposite end of the heat exchange channels;
  a plurality of secondary plates subdividing the heat exchange channels into preheat channels and combustion channels;
  means for retaining a solid catalyst in the reaction channels;
  means for retaining a solid catalyst in the combustion channels;
  a heating fluid conduit for communicating the reactant outlet;
  a combustor defined by the heating fluid conduit or the heat exchange channel; and,
  an oxygen conduit for supplying an oxygen containing fluid to the combustor.

16. The apparatus of claim 15 wherein the channels have an average width of less than 1 inch.

17. The apparatus of claim 16 wherein each reactant outlet communicates with at least two heating fluid inlets and the outlet of each preheat channel communicates with at least two reactant inlets.

18. The apparatus of claim 15 wherein the plates are flat.

19. The apparatus of claim 15 wherein the heat exchange channels define the combustor.

20. The apparatus of claim 15 wherein a plurality of secondary plates subdivide the heat exchange channels to define a central preheat channel bordered on each side by a combustion channel and a preheat conduit communicates an outlet of the preheat channel with the inlet of the reaction channel.

21. The apparatus of claim 15 wherein the plates define corrugations and the corrugations maintain the spacing of the plates.

22. An apparatus for contacting reactants in a reaction stream with a catalyst in a reaction zone while directly heating reactants by combusting a portion of the reaction stream or components produced in the reaction zone in a heating zone while indirectly heating the reactants by contact with combustion gases formed in the heating zone, the apparatus comprising:
  a reactor body;
  a primary plate in the reactor body defining a first reactor volume with a first plurality of pockets on a first side of the plate and defining a second reactor volume with a second plurality of pockets on a second side of the plate;
  one or more first divider plates located in the reactor body and extending into at least two pockets in the first plurality of pockets to define at least two pairs of interconnected channels along a first flow path;
  one or more second divider plates located in the reactor body and extending into at least two pockets in the second plurality of pockets to define at least two pairs of interconnected channels along a second flow path;
  an inlet and an outlet for the first flow path defined by the reactor body;
  an inlet and an outlet for the second flow path defined by the reactor body;
  and a heat exchange surface provided by at least the primary plate or the first or second divider plates.

23. The apparatus of claim 22 wherein a catalyst coating covers the surface of at least one of the primary plate or the first or second divider plates.

24. The apparatus of claim 22 wherein the primary plate and at least one of the divider plate define a manifold volume along the first or second path length and a conduit extends into the manifold volume to inject a fluid therein.

25. The apparatus of claim 22 wherein the primary plate has a serpentine shape and a divider plate extends into each loop of the defined by the primary plate.

26. The apparatus of claim 25 wherein at least one divider plate has a perforated portion at the end positioned adjacent to the primary plate.

27. The apparatus of claim 25 wherein at least all of the divider plates in one of the first or second plurality of divider plates are fixed to a common support plate and the common support is adapted for removal from the reactor body.

* * * * *